(12) United States Patent
Schwartz et al.

(10) Patent No.: US 8,889,081 B2
(45) Date of Patent: Nov. 18, 2014

(54) ROOM FOGGING DISINFECTION SYSTEM

(75) Inventors: Mason Schwartz, Elk River, MN (US);
Thomas M. Gentle, Saint Michael, MN (US); Michael P. Petersen, Eden Prairie, MN (US)

(73) Assignee: Medivators Inc., Minneapolis, MN (US)

( * ) Notice: Subject to any disclaimer, the term of this patent is extended or adjusted under 35 U.S.C. 154(b) by 580 days.

(21) Appl. No.: 12/904,415

(22) Filed: Oct. 14, 2010

(65) Prior Publication Data

US 2011/0091354 A1   Apr. 21, 2011

Related U.S. Application Data

(60) Provisional application No. 61/252,011, filed on Oct. 15, 2009, provisional application No. 61/260,466, filed on Nov. 12, 2009.

(51) Int. Cl.
| | |
|---|---|
| *A61L 2/00* | (2006.01) |
| *G05D 7/00* | (2006.01) |
| *A61L 2/18* | (2006.01) |
| *A61L 2/22* | (2006.01) |
| *A61L 9/14* | (2006.01) |
| *F24F 3/16* | (2006.01) |

(52) U.S. Cl.
CPC ............... *F24F 3/16* (2013.01); *A61L 2202/25* (2013.01); *A61L 2202/16* (2013.01); *A61L 2209/135* (2013.01); *A61L 2/22* (2013.01); *A61L 2202/11* (2013.01); *A61L 2202/14* (2013.01); *F24F 2003/1675* (2013.01); *A61L 2209/21* (2013.01); *A61L 9/14* (2013.01); *A61L 2202/15* (2013.01); *A61L 2209/14* (2013.01); *A61L 2209/111* (2013.01)
USPC ............................. 422/292; 422/28; 422/111

(58) Field of Classification Search
CPC .................................... A61L 2/22; A61L 9/14
USPC ............................................ 422/28, 111, 292
See application file for complete search history.

(56) References Cited

U.S. PATENT DOCUMENTS

| | | |
|---|---|---|
| 1,032,404 A | 5/1913 | Kiefer |
| 1,062,404 A | 5/1913 | Kiefer |

(Continued)

FOREIGN PATENT DOCUMENTS

| | | |
|---|---|---|
| EP | 0302420 A2 | 2/1989 |
| EP | 0774263 A1 | 5/1997 |

(Continued)

OTHER PUBLICATIONS

International Search Report and Written Opinion issued in PCT/US2012/039160, mailed Oct. 2, 2012.

(Continued)

*Primary Examiner* — Kevin Joyner
(74) *Attorney, Agent, or Firm* — Faegre Baker Daniels

(57) ABSTRACT

A system for disinfecting a room includes an enclosure having first and second air inlets and an air intake control assembly to selectably control air flow into the enclosure through the first and second air inlets. Air that flows between the exterior and interior of the enclosure through the second air inlet passes through a filter assembly. The enclosure also includes an air dispersion outlet having a fan that draws air into the enclosure through the first and second air inlets and forces air out of the enclosure. A chemical dispersion assembly generates a disinfecting fog relative to the fan. A system controller controls the air intake control assembly to disperse the disinfecting fog into the room, and subsequently draw the disinfecting fog from the room and through the filter assembly.

29 Claims, 7 Drawing Sheets

(56) References Cited

U.S. PATENT DOCUMENTS

| | | | |
|---|---|---|---|
| 1,114,880 A | 10/1914 | Hall | |
| 1,837,264 A | 12/1931 | Hackley | |
| 2,965,936 A | 6/1957 | Kaye | |
| 2,836,570 A | 5/1958 | Peers | |
| 3,054,270 A | 8/1960 | Huston | |
| 3,114,599 A | 12/1963 | Fanning | |
| 3,436,173 A | 4/1969 | Power | |
| 3,498,742 A | 3/1970 | Long | |
| 3,547,576 A | 12/1970 | Sheikh | |
| 3,816,074 A | 6/1974 | Decupper | |
| 3,839,841 A | 10/1974 | Amplatz | |
| 3,936,270 A | 2/1976 | Gunther | |
| 3,958,935 A | 5/1976 | Kowol | |
| 4,064,062 A | 12/1977 | Yurko | |
| 4,119,400 A | 10/1978 | Kurz | |
| 4,169,123 A | 9/1979 | Moore et al. | |
| 4,169,124 A | 9/1979 | Forstrom et al. | |
| 4,230,663 A | 10/1980 | Forstrom et al. | |
| 4,241,010 A | 12/1980 | Baran | |
| 4,241,020 A | 12/1980 | Grantham | |
| 4,249,265 A | 2/1981 | Coester | |
| 4,259,103 A | 3/1981 | Malek et al. | |
| 4,270,658 A | 6/1981 | Schuster | |
| 4,294,804 A | 10/1981 | Baran | |
| 4,366,125 A | 12/1982 | Kodera et al. | |
| 4,447,399 A | 5/1984 | Runnells et al. | |
| 4,457,892 A | 7/1984 | Young | |
| 4,483,771 A * | 11/1984 | Koch | 210/490 |
| 4,512,951 A | 4/1985 | Koubek | |
| 4,587,264 A | 5/1986 | Jourdan-Laforte et al. | |
| 4,592,896 A | 6/1986 | Runnells et al. | |
| 4,637,916 A | 1/1987 | Hennebert et al. | |
| 4,643,876 A | 2/1987 | Jacobs et al. | |
| 4,687,635 A | 8/1987 | Kaehler et al. | |
| 4,744,951 A | 5/1988 | Cummings et al. | |
| 4,756,882 A | 7/1988 | Jacobs et al. | |
| 4,843,867 A | 7/1989 | Cummings | |
| 4,892,705 A | 1/1990 | Sternfeld et al. | |
| 4,921,675 A | 5/1990 | Johnson | |
| 4,943,414 A | 7/1990 | Jacobs et al. | |
| 4,952,370 A | 8/1990 | Cummings et al. | |
| 4,956,145 A | 9/1990 | Cummings et al. | |
| 4,986,963 A | 1/1991 | Corcoran et al. | |
| 5,008,079 A | 4/1991 | Wutzler et al. | |
| 5,258,162 A | 11/1993 | Andersson et al. | |
| 5,340,878 A | 8/1994 | Sadatoshi et al. | |
| 5,460,962 A | 10/1995 | Kemp | |
| 5,482,683 A | 1/1996 | Sheth et al. | |
| 5,508,009 A | 4/1996 | Rickloff et al. | |
| 5,512,244 A | 4/1996 | Griffiths et al. | |
| 5,527,508 A | 6/1996 | Childers et al. | |
| 5,534,221 A | 7/1996 | Hillebrenner et al. | |
| 5,556,607 A | 9/1996 | Childers et al. | |
| 5,580,530 A | 12/1996 | Kowatsch et al. | |
| 5,620,656 A | 4/1997 | Wensky et al. | |
| 5,641,455 A | 6/1997 | Rosenlund et al. | |
| 5,667,753 A | 9/1997 | Jacobs et al. | |
| 5,674,450 A | 10/1997 | Lin et al. | |
| 5,676,837 A | 10/1997 | Jungbauer et al. | |
| 5,733,503 A | 3/1998 | Kowatsch et al. | |
| 5,741,460 A | 4/1998 | Jacob et al. | |
| 5,779,973 A | 7/1998 | Edwards et al. | |
| 5,784,934 A | 7/1998 | Izumisawa | |
| 5,792,422 A | 8/1998 | Lin et al. | |
| 5,801,010 A | 9/1998 | Falkowski et al. | |
| 5,834,313 A | 11/1998 | Lin | |
| 5,847,393 A | 12/1998 | Van Den Berg et al. | |
| 5,851,483 A | 12/1998 | Nicolle et al. | |
| 5,863,499 A | 1/1999 | Kralovic | |
| 5,869,000 A | 2/1999 | DeCato | |
| 5,876,666 A | 3/1999 | Lin et al. | |
| D408,837 S | 4/1999 | Gotham et al. | |
| 5,902,413 A | 5/1999 | Puszko et al. | |
| 5,904,901 A * | 5/1999 | Shimono et al. | 422/120 |
| 5,906,794 A | 5/1999 | Childers | |
| 5,955,025 A | 9/1999 | Barrett | |
| 5,961,921 A | 10/1999 | Addy et al. | |
| 5,980,825 A | 11/1999 | Addy et al. | |
| 6,010,662 A | 1/2000 | Lin et al. | |
| 6,030,579 A | 2/2000 | Addy et al. | |
| 6,036,918 A | 3/2000 | Kowanko | |
| 6,039,922 A | 3/2000 | Swank et al. | |
| 6,041,794 A | 3/2000 | Lin et al. | |
| 6,066,294 A | 5/2000 | Lin et al. | |
| 6,094,887 A | 8/2000 | Swank et al. | |
| 6,096,265 A | 8/2000 | Mezger et al. | |
| 6,096,266 A | 8/2000 | Duroselle | |
| 6,120,730 A | 9/2000 | Swank et al. | |
| 6,135,433 A | 10/2000 | Nurmi | |
| 6,162,394 A | 12/2000 | Nicolle et al. | |
| 6,162,395 A | 12/2000 | Kowanko | |
| 6,183,691 B1 | 2/2001 | Swank et al. | |
| D438,980 S | 3/2001 | Hehenberger | |
| 6,234,310 B1 | 5/2001 | Goldhaber | |
| 6,269,680 B1 | 8/2001 | Prieve et al. | |
| 6,286,527 B1 | 9/2001 | Stanley | |
| 6,312,645 B1 | 11/2001 | Lin et al. | |
| 6,312,646 B2 | 11/2001 | Kowanko | |
| 6,354,312 B1 | 3/2002 | Lin et al. | |
| 6,365,102 B1 | 4/2002 | Wu et al. | |
| 6,365,103 B1 | 4/2002 | Fournier | |
| 6,391,260 B1 | 5/2002 | Davis et al. | |
| 6,406,666 B1 | 6/2002 | Cicha et al. | |
| 6,439,246 B2 | 8/2002 | Stanley | |
| 6,451,254 B1 | 9/2002 | Wang et al. | |
| 6,468,472 B1 | 10/2002 | Yu et al. | |
| 6,495,100 B1 | 12/2002 | Lin et al. | |
| 6,528,017 B2 | 3/2003 | Jacobs et al. | |
| 6,530,399 B2 | 3/2003 | Nguyen et al. | |
| 6,582,654 B1 | 6/2003 | Kral et al. | |
| 6,594,971 B1 | 7/2003 | Addy et al. | |
| 6,596,231 B1 | 7/2003 | Catelli et al. | |
| 6,600,444 B2 | 7/2003 | Desjardins | |
| 6,641,781 B2 | 11/2003 | Walta | |
| 6,673,313 B2 | 1/2004 | Wang et al. | |
| 6,746,647 B2 | 6/2004 | Kohler et al. | |
| 6,790,410 B2 | 9/2004 | Metzner et al. | |
| 6,797,234 B2 | 9/2004 | Stanley | |
| 6,884,392 B2 | 4/2005 | Malkin et al. | |
| 6,977,061 B2 | 12/2005 | Lin et al. | |
| 6,998,582 B1 | 2/2006 | Maroti | |
| 7,001,873 B2 | 2/2006 | McDonnell et al. | |
| 7,005,549 B2 | 2/2006 | Hobson et al. | |
| 7,025,932 B2 | 4/2006 | Martin et al. | |
| 7,146,746 B2 | 12/2006 | Kawasaki | |
| 7,178,555 B2 | 2/2007 | Engel et al. | |
| 7,179,419 B2 | 2/2007 | Lin et al. | |
| 7,186,371 B1 | 3/2007 | Watling | |
| 7,186,372 B2 | 3/2007 | Kohler et al. | |
| 7,186,374 B2 | 3/2007 | Zelina et al. | |
| 7,294,305 B2 | 11/2007 | Lin et al. | |
| 7,303,073 B2 | 12/2007 | Raynal-Olive et al. | |
| 7,307,191 B2 | 12/2007 | Hobson et al. | |
| 7,326,382 B2 | 2/2008 | Adiga et al. | |
| 7,434,372 B2 | 10/2008 | Vanhamel et al. | |
| 7,449,145 B2 | 11/2008 | Kohler et al. | |
| 7,452,504 B2 | 11/2008 | Wu et al. | |
| 7,468,159 B2 | 12/2008 | Lin et al. | |
| 7,491,371 B2 | 2/2009 | Moller et al. | |
| 7,541,002 B2 | 6/2009 | Centanni | |
| 7,556,767 B2 | 7/2009 | Lin et al. | |
| 7,569,180 B2 | 8/2009 | Kohler et al. | |
| 7,578,969 B2 | 8/2009 | Mielnik et al. | |
| 7,604,773 B2 | 10/2009 | Ekstrom et al. | |
| 7,608,218 B2 | 10/2009 | Fryer et al. | |
| 7,611,667 B2 | 11/2009 | Centanni | |
| 7,615,187 B2 | 11/2009 | Helton et al. | |
| 7,622,074 B2 | 11/2009 | Mielnik | |
| 7,651,667 B2 | 1/2010 | McVey et al. | |
| 7,670,550 B2 | 3/2010 | Lin et al. | |
| 7,670,565 B2 | 3/2010 | McVey et al. | |
| 7,678,339 B2 | 3/2010 | Wira | |
| 7,713,473 B2 | 5/2010 | Kendall et al. | |
| 7,718,122 B2 | 5/2010 | Smith et al. | |

(56) References Cited

U.S. PATENT DOCUMENTS

| | | |
|---|---|---|
| 7,803,315 B2 | 9/2010 | McDonnell et al. |
| 7,807,100 B2 | 10/2010 | Choperena et al. |
| 7,811,531 B2 | 10/2010 | Mielnik et al. |
| 7,850,925 B2 | 12/2010 | Centanni et al. |
| 7,988,911 B2 | 8/2011 | Centanni et al. |
| 7,988,920 B2 | 8/2011 | Centanni et al. |
| 7,993,602 B2 | 8/2011 | Moriyama et al. |
| 8,012,424 B2 | 9/2011 | Jethrow et al. |
| 8,025,848 B2 | 9/2011 | McVey et al. |
| 8,056,719 B2 | 11/2011 | Porret et al. |
| 8,062,590 B1 | 11/2011 | Ricciardi et al. |
| 8,110,156 B2 | 2/2012 | Ricciardi et al. |
| 8,128,789 B2 | 3/2012 | Hirata et al. |
| 8,133,437 B2 | 3/2012 | Scalzo et al. |
| 8,178,357 B2 | 5/2012 | Trogler et al. |
| 8,236,240 B2 | 8/2012 | Childers et al. |
| 8,298,482 B2 | 10/2012 | Rees et al. |
| 8,343,422 B2 | 1/2013 | Sato et al. |
| 8,343,437 B2 | 1/2013 | Patel |
| 8,357,331 B2 | 1/2013 | McVey et al. |
| 8,425,837 B2 | 4/2013 | Carbone et al. |
| 8,444,919 B2 | 5/2013 | Erickson |
| 2001/0000227 A1 | 4/2001 | Kowanko |
| 2001/0036422 A1 | 11/2001 | Lin et al. |
| 2001/0053333 A1 | 12/2001 | Messier et al. |
| 2002/0069616 A1 | 6/2002 | Odell et al. |
| 2002/0081228 A1 | 6/2002 | Hui et al. |
| 2002/0085950 A1 | 7/2002 | Robitaille et al. |
| 2002/0114727 A1* | 8/2002 | McVey et al. ............ 422/4 |
| 2002/0122744 A1 | 9/2002 | Hui et al. |
| 2002/0168289 A1 | 11/2002 | McVey |
| 2002/0187067 A1 | 12/2002 | Lukasik et al. |
| 2003/0017074 A1 | 1/2003 | Wang et al. |
| 2003/0086820 A1 | 5/2003 | McDonnell et al. |
| 2003/0124026 A1 | 7/2003 | Williams et al. |
| 2003/0138347 A1 | 7/2003 | Lin |
| 2003/0190253 A1 | 10/2003 | Kohler et al. |
| 2003/0235511 A1 | 12/2003 | Jacobs et al. |
| 2004/0001776 A1 | 1/2004 | Fryer et al. |
| 2004/0005240 A1 | 1/2004 | Adiga et al. |
| 2004/0005259 A1 | 1/2004 | Sacca |
| 2004/0022671 A1 | 2/2004 | Malatesta |
| 2004/0022673 A1* | 2/2004 | Protic ............... 422/28 |
| 2004/0028556 A1 | 2/2004 | Frost et al. |
| 2004/0052679 A1 | 3/2004 | Root et al. |
| 2004/0081601 A1 | 4/2004 | Morrissey et al. |
| 2004/0162228 A1 | 8/2004 | Hobson et al. |
| 2004/0170527 A1 | 9/2004 | Jacobs et al. |
| 2004/0184950 A1* | 9/2004 | McVey et al. ............ 422/4 |
| 2005/0013726 A1 | 1/2005 | Hill et al. |
| 2005/0042130 A1 | 2/2005 | Lin et al. |
| 2005/0084431 A1 | 4/2005 | Hill et al. |
| 2005/0147527 A1 | 7/2005 | Brown et al. |
| 2005/0196313 A1 | 9/2005 | Choperena et al. |
| 2005/0252274 A1 | 11/2005 | Centanni |
| 2005/0260097 A1 | 11/2005 | Williams et al. |
| 2006/0078459 A1 | 4/2006 | Kohler et al. |
| 2006/0088441 A1 | 4/2006 | Hill |
| 2006/0099106 A1 | 5/2006 | Watling et al. |
| 2007/0003431 A1 | 1/2007 | Kendall et al. |
| 2007/0014691 A1 | 1/2007 | Lin et al. |
| 2007/0034095 A1* | 2/2007 | McDonnell et al. ......... 99/468 |
| 2007/0053813 A1 | 3/2007 | Martin |
| 2007/0092398 A1 | 4/2007 | McDonald |
| 2007/0098592 A1* | 5/2007 | Buczynski et al. ............ 422/3 |
| 2007/0160491 A1 | 7/2007 | Kohler et al. |
| 2007/0207054 A1 | 9/2007 | Langford |
| 2007/0253859 A1 | 11/2007 | Hill |
| 2008/0240981 A1 | 10/2008 | Berentsveig et al. |
| 2009/0209031 A1 | 8/2009 | Stopek |
| 2009/0324445 A1 | 12/2009 | Kohler et al. |
| 2010/0011823 A1 | 1/2010 | Dahms et al. |
| 2010/0028200 A1 | 2/2010 | Shiosawa |
| 2010/0034697 A1 | 2/2010 | Weinberger et al. |
| 2010/0034707 A1 | 2/2010 | Mielnik et al. |
| 2010/0143218 A1 | 6/2010 | Nurminen et al. |
| 2010/0196197 A1 | 8/2010 | Rovison, Jr. et al. |
| 2010/0226821 A1 | 9/2010 | Ricciardi et al. |
| 2010/0296969 A1 | 11/2010 | Ngo et al. |
| 2010/0297776 A1 | 11/2010 | Trogler et al. |
| 2010/0303671 A1 | 12/2010 | Bertrand |
| 2010/0316527 A1 | 12/2010 | McLaren et al. |
| 2011/0044851 A1 | 2/2011 | Centanni et al. |
| 2011/0044852 A1 | 2/2011 | Ryan et al. |
| 2011/0052449 A1 | 3/2011 | Centanni et al. |
| 2011/0076189 A1 | 3/2011 | McVey et al. |
| 2011/0076192 A1 | 3/2011 | Robitaille et al. |
| 2011/0079525 A1 | 4/2011 | Peck et al. |
| 2011/0135537 A1 | 6/2011 | Schwartz et al. |
| 2011/0165299 A1 | 7/2011 | Sato et al. |
| 2011/0182772 A1 | 7/2011 | Holt |
| 2012/0009085 A1 | 1/2012 | Burger |
| 2012/0189494 A1 | 7/2012 | Rovison, Jr. et al. |
| 2012/0219456 A1 | 8/2012 | Childers et al. |
| 2012/0277662 A1 | 11/2012 | Golkowski |
| 2012/0301356 A1 | 11/2012 | Olson et al. |
| 2013/0065958 A1 | 3/2013 | Dunn |
| 2013/0101462 A1 | 4/2013 | Keil |

FOREIGN PATENT DOCUMENTS

| | | |
|---|---|---|
| EP | 0923951 B1 | 6/1999 |
| EP | 1378253 A1 | 1/2004 |
| EP | 1481692 B1 | 12/2004 |
| EP | 1813220 A1 | 8/2007 |
| EP | 1473044 B1 | 12/2007 |
| EP | 1171368 B1 | 2/2008 |
| EP | 1935515 A2 | 6/2008 |
| EP | 1308173 B1 | 12/2008 |
| EP | 1110557 B1 | 3/2009 |
| EP | 2228076 A1 | 9/2010 |
| JP | 08126605 A | 5/1996 |
| JP | 11015570 A | 1/1999 |
| JP | 11137650 A | 5/1999 |
| JP | 2002508219 A | 3/2002 |
| JP | 2003260118 A | 9/2003 |
| JP | 2005143669 A | 6/2005 |
| JP | 2007167546 A | 7/2007 |
| JP | 2009513213 A | 4/2009 |
| JP | 2009131296 A | 6/2009 |
| JP | 2009268466 A | 11/2009 |
| WO | 0207788 | 1/2002 |
| WO | WO0249682 A1 | 6/2002 |
| WO | 2007008205 | 1/2007 |
| WO | WO2007049076 A1 | 5/2007 |
| WO | 2008014615 | 2/2008 |
| WO | WO2012128734 A1 | 9/2012 |

OTHER PUBLICATIONS

International Search Report and Written Opinion issued in PCT/US2010/052622, mailed Jan. 20, 2011, 14 pages.

"Cantel Subsidiary Receives Expanded EPO Approval for Minncare Cold Sterilant in Fogging Applications", Business Wire, Jul. 4, 2008, 1 page.

International Search Report and Written Opinion issued in PCT/US2010/058885, mailed Feb. 10, 2011, 11 pages.

International Standard, ISO 11140-1, 2nd Edition Jul. 15, 2005, Sterilization of Health Care Products—Chemical Indicators—Part 1: General Requirements, pp. 1-27.

Minncare Dry Fog™ System: An Integral part of Modern Cleanroom Disinfection Procedures, © 2009 Mar Cor Purification, 4 pages.

Portner, Dorothy M. et al., "Sporicidal Effect of Peracetic Acid Vapor", Applied Microbiology, vol. 16, No. 11, Nov. 1968, pp. 1782-1785.

Rutala, William A. et al., "New Disinfection and Sterilization Methods", Emerging Infectious Diseases Journal, vol. 7, No. 2, Mar.-Apr. 2001, 14 pages.

The Mini Fog System: A Modern Method to Enhance Small Space Disinfection, © 2008 Mar Cor Purification, 2 pages.

European Search Report issued in EP Application No. 13152441, mailed Feb. 27, 2013, 8 pages.

(56) References Cited

OTHER PUBLICATIONS

FMC Material Safety Data Sheet, Date Approved Nov. 10, 2006, 11 pages.

Lunger, MJ et al., "Reducing Pump-Down Time With Dry Air Venting", 43rd Annual Technical Conference Proceedings, Denver, Apr. 15-20, 2000, 1 page.

* cited by examiner

ROOM FOGGING DISINFECTION SYSTEM

CROSS-REFERENCE TO RELATED APPLICATIONS

This application claims priority to Provisional Application No. 61/252,011, filed Oct. 15, 2009, and to Provisional Application No. 61/260,466, filed Nov. 12, 2009, which are incorporated herein by reference in their entireties.

TECHNICAL FIELD

The present invention relates to disinfection systems. More particularly, the present invention relates to a system for disinfecting a room.

BACKGROUND

With the growing need for microbiological clean environments, room disinfection is an important part of maintaining a microbiologically clean environment for a variety of purposes: manufacturing, employee safety in research environments, patient safety in hospitals, and contamination control in areas such as schools, locker rooms, child care facilities, and the like.

Cleanroom disinfection is a routine procedure in many pharmaceutical, biotech, cosmetic, and other microbiology industries. These industries are dependent on microbiologically clean areas primarily for production and R&D. Additionally, some industries are governed by regulatory bodies that impose standards for microbiological cleanliness and set requirements for regular, certified biodecontamination of certain areas. Pharmaceutical facilities have a number of areas that require regular disinfection procedures in order to provide a microbiologically clean environment. Some example biodecontamination procedures include annual shutdown biodecontamination, commissioning biodecontamination, decommissioning biodecontamination of areas used for pathogen work, eradication of problematic microorganisms from production lines and laboratory areas, emergency biodecontamination for accidental release or spillage of microorganisms, regular cleanroom biodecontamination, and isolator and pass-through biodecontamination.

SUMMARY

The present invention relates to a system for disinfecting a room including an enclosure having first and second air inlets, and an air intake control assembly configured for selectable control of air flow between an exterior and an interior of the enclosure through the first and second air inlets. A filter assembly is disposed relative to the second air inlet such that air that flows between the exterior and interior of the enclosure through the second air inlet passes through the filter assembly. An air dispersion outlet including a fan is configured to draw air into the enclosure through the first and second air inlets and to force air out of the enclosure. A chemical dispersion assembly is configured to generate a disinfecting fog in the interior of the enclosure. A system controller is configured to open the first air inlet and activate the fan to disperse the disinfecting fog into the room, and subsequently close the first air inlet and activate the fan to draw the disinfecting fog from the room and through the filter assembly.

In another aspect, the present invention relates to a method for disinfecting a room. A disinfecting fog is generated in an enclosure including a first air inlet, a second air inlet, and an air dispersion outlet having a fan configured to draw air into the enclosure through the first and second air inlets and to force air out of the enclosure. The enclosure further includes a filter assembly disposed relative to the second air inlet such that air that flows between the exterior and interior of the enclosure through the second air inlet passes through the filter assembly. An air intake control assembly is actuated to open the first air inlet, and the fan is activated to draw air through the first air inlet and out of the air dispersion outlet to disperse the fog into the room. The air intake control assembly is then actuated to close the first air inlet to draw the fog from the room through the second air inlet and the filter assembly. After the fog has been removed from the room, the fan is deactivated.

In a further aspect, the present invention relates to a system for disinfecting a room including an enclosure having first and second air inlets and a plurality of controllable louvers arranged to control of air flow between an exterior and an interior of the enclosure through the first and second air inlets. A vapor destruction assembly is disposed relative to the second air inlet such that air that flows between the exterior and interior of the enclosure through the second air inlet passes through the vapor destruction assembly. An air dispersion outlet including a fan is configured to draw air into the enclosure through the first and second air inlets and to force air out of the enclosure. A chemical dispersion assembly is configured to generate a disinfecting fog relative to the air dispersion assembly. A system controller is configured to open the plurality of louvers and activate the fan to disperse the disinfecting fog into the room, and to subsequently close the plurality of louvers to draw the disinfecting fog from the room and through the filter assembly.

In some embodiments, while the disinfecting fog is being dispersed, or after the disinfecting fog is drawn from the room through the filter assembly, the system is configured to disperse an antimicrobial coating substance into the room to coat surfaces in the room. For example, the antimicrobial coating substance may be dispensed relative to the fan to disperse the antimicrobial coating substance into the room.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
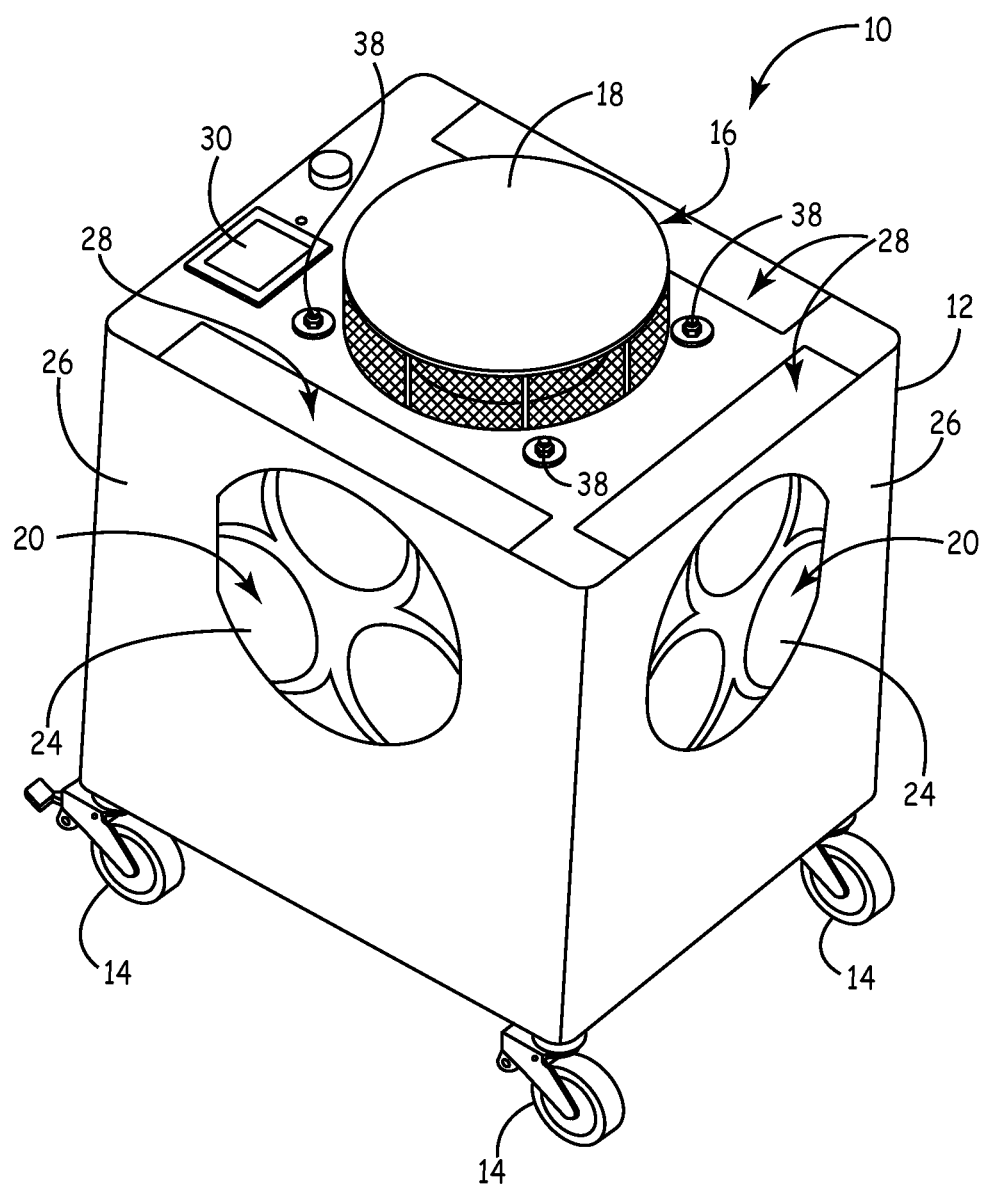
FIG. 1 is a perspective view a system for disinfecting a room according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 2:
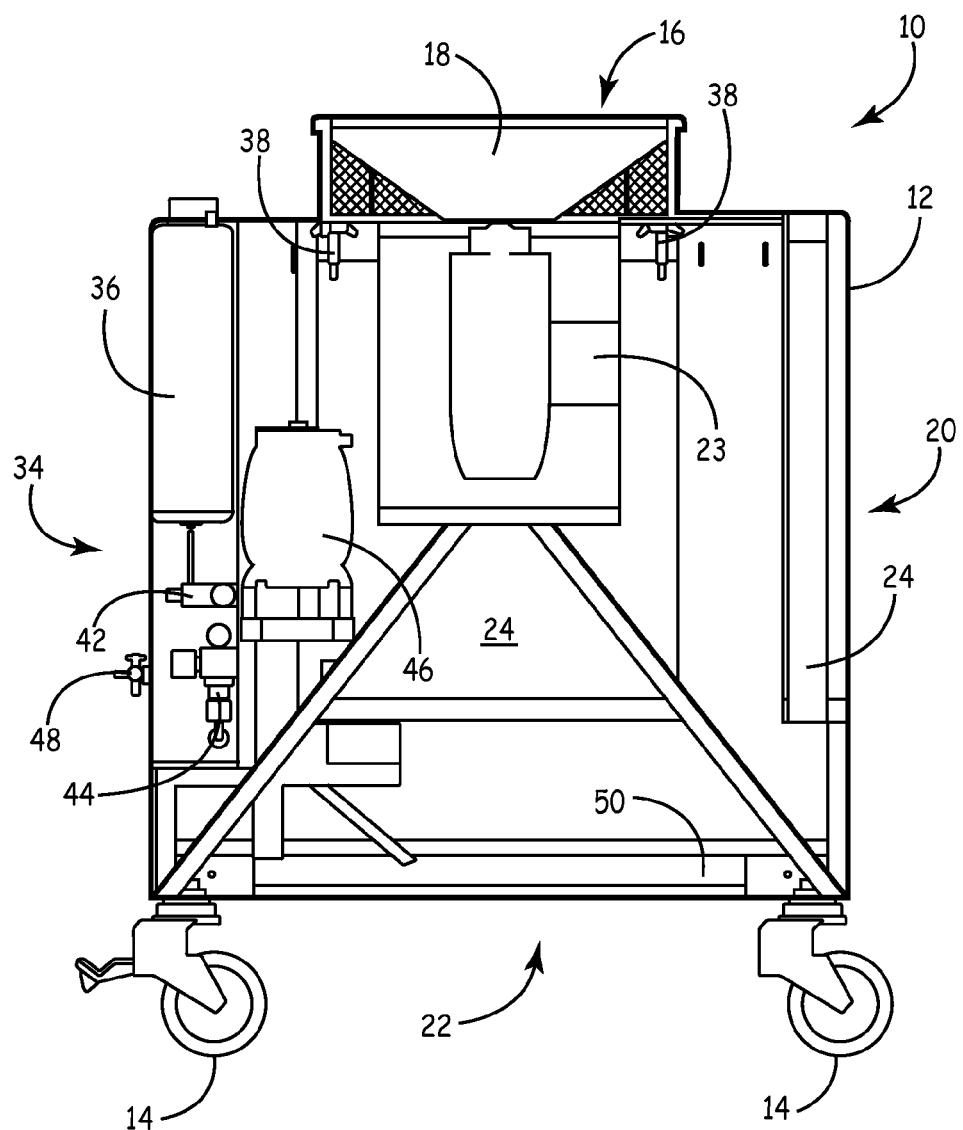
FIG. 2 is a side cross-sectional view of the system shown in FIG. 1, illustrating portions of the interior of the system.
Figure 3:
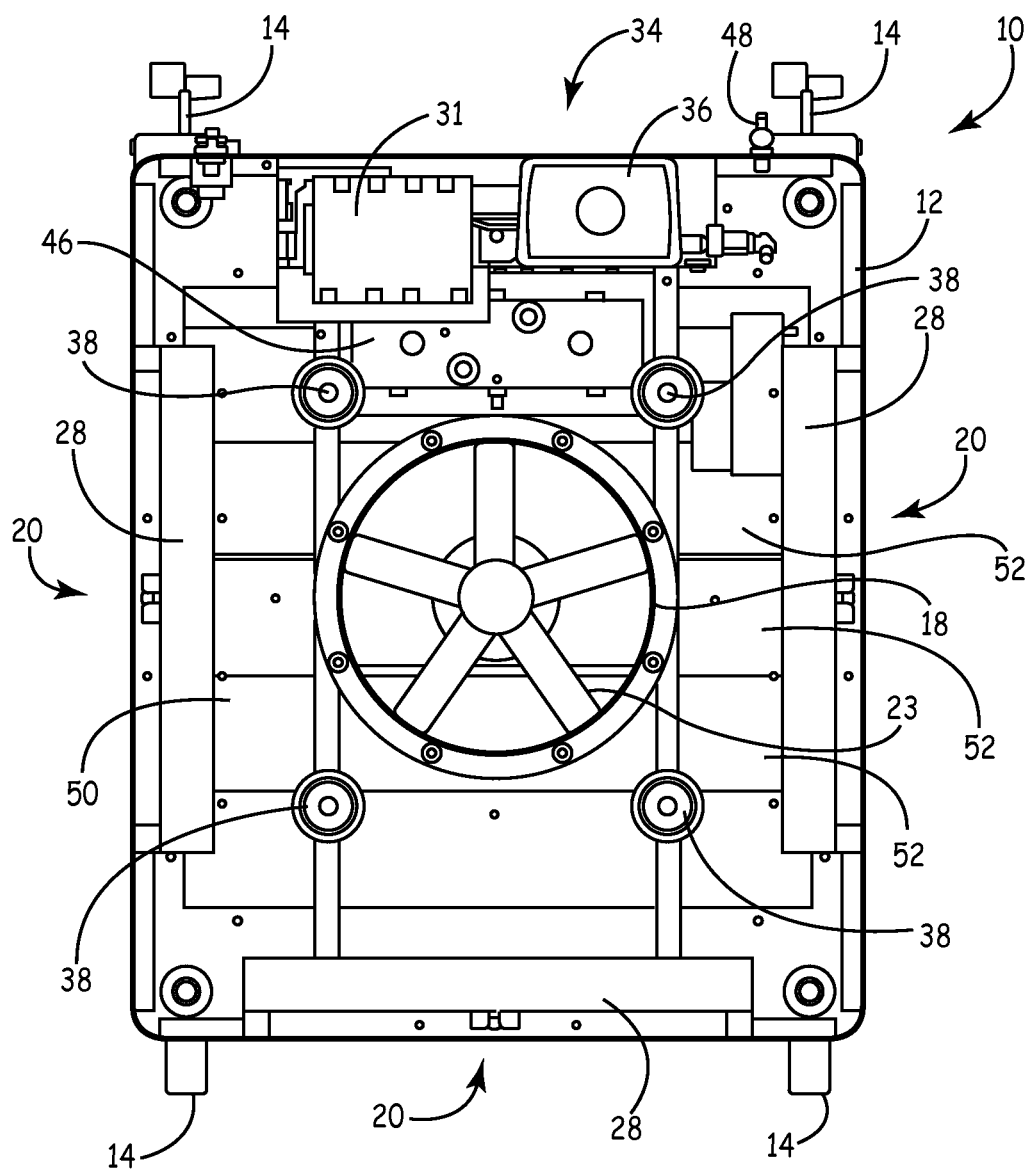
FIG. 3 is a top cross-sectional view of the system shown in FIG. 1, illustrating portions of the interior of the system.

FIG. 1 is a perspective view, FIG. 2 is a side cross-sectional view, and FIG. 3 is a top cross-sectional view, of a system 10 for disinfecting a room according to an embodiment of the present invention. The system 10 includes a housing 12 that includes wheels 14 for transportation to the room to be disinfected. In the embodiment shown, the housing 12 is a box-like metal enclosure, but other configurations for the housing 12 are also possible. The housing 12 includes an air dispersion outlet 16 having an air dispersion assembly 18, a plurality of side air inlets 20, and a bottom air inlet 22.

The air dispersion outlet 16 includes a fan 23 that, when activated, draws air through either of side air inlets 20 and bottom air inlet 22 into the interior of the housing 12. The fan 23 also draws air from the interior of the housing 12 through the air dispersion outlet 16 and forces the air through the air dispersion assembly 18. The air dispersion assembly 18 is configured to disperse or spread the air throughout the room to be disinfected. In some embodiments, the air dispersion assembly 18 comprises a plurality of parallel panels that are angled with respect to the top of the housing 12. In other embodiments, the air dispersion assembly 18 comprises an air diffuser mounted to the fan 23.

The side air inlets 20 are disposed on the four sides that connect the top and bottom of the housing 12 in the embodiment shown. In alternative configurations, the side air inlets 20 may be provided on fewer than four sides of the housing 12. The side air inlets 20 are configured to allow air to flow between the exterior and interior of the housing 12. The shape and size of the side air inlets 20 may be designed to control the rate at which the air flows between the exterior and interior of the housing 12. In the embodiment shown, a filter 24 is arranged relative to each of the side air inlets 20 such that air drawn through the side air inlets 20 passes through the filters 24. Filter covers 26 secured to the outside of the housing 12 cover the filters 24 to protect the filters 24 from damage during transportation of the system 10. Filter doors 28 at the top of the housing 12 provide access to slots that retain the filters 24 to, for example, allow replacement of the filters 24. In alternative embodiments, the system 10 includes one or more air outlets with a filter arranged relative thereto.

The bottom air inlet 22 is disposed on the side of the housing 12 that faces the floor or ground in the embodiment shown. Alternatively, one or more air inlets that perform functions similar to bottom air inlet 22 may be located on a side and/or top of the housing 12. The bottom air inlet 22 is configured to allow air to flow between the exterior and interior of the housing 12. The positioning of the bottom air inlet 22 a distance above the floor assures that the disinfection also occurs beneath the system 10. In some embodiments, the bottom air inlet 22 does not include a filter such that air flows directly between the exterior and interior of the housing 12. The shape and size of the bottom air inlets 22 may be designed to control the rate at which the air flows between the exterior and interior of the housing 12.

A user interface 30 is provided on the top of the housing 12 to provide a means for a user to control and activate the system 10. The user interface 30 communicates with a system controller 31. In some embodiments, the user interface 30 is a button or other actuatable mechanism that allows a user to enable the system after locating the system 10 in the room to be disinfected. The user interface 30 may also include a display and/or other input devices to allow the user to select different programs and control settings of the system 10, for example. In the embodiment shown, the user interface 30 includes a touch screen, but the user interface may include other types of input devices, such as a keyboard. The user interface 30 may further include a remote control that communicates wirelessly with the system controller 31 via an antenna or other transceiver. The remote control may be configured for one-way or two-way communication with the system controller 31. In a two-way communication configuration, the remote control can display information about the status of the system 10 and the disinfection process to the user. The antenna or transceiver on the system 10 may also be configured for long-range communication, such as communication via satellite, cellular, or radio frequency signals, or over the Internet.

The system 10 also includes a chemical dispersion assembly 34. The chemical dispersion assembly 34 may include one or more chemical reservoirs 36 in the interior of the housing 12 that are configured to retain substance(s) to be dispersed into the room to be disinfected during operation of the system 10. The one or more chemical reservoirs 36 may be holding tanks or other containers, for example. In some embodiments, the chemical dispersion assembly 34 includes a disinfecting substance reservoir and an antimicrobial coating substance reservoir. In other embodiments, the disinfecting substance and the antimicrobial coating substance are combined in a single reservoir. In still other embodiments, two or more substances are retained in separate reservoirs and are combined prior to dispersing into the room (e.g., by mixing into a reservoir or by combining at the point of dispersement). The chemical dispersion assembly 34 may also retain other substances to be dispersed before, during, or after dispersement of the disinfecting substance including, but not limited to, a surfactant, an anti-corrosive agent, a buffer substance, water, a disinfectant and/or antimicrobial coating destruct chemical, and/or a fragrance. The disinfecting substance may be a room temperature (e.g., 20° C. to 25° C.) substance that can be dispersed as a fog during operation of the system 10. In other embodiments, the disinfecting substance may be used at temperatures in the range of between about −40° C. to 100° C. In some embodiments, the disinfecting substance includes peracetic acid (PAA), peracitric acid, hydrogen peroxide ($H_2O_2$), hospital grade disinfectants, and/or antimicrobial solution.

In order to prepare the disinfecting substance for dispersion into the interior of the housing 12, the chemical dispersion assembly 34 may include one or more appropriate nozzles 38 or other components in fluid communication with the chemical reservoirs 36. The chemical dispersion assembly 34 may also include a dispersion system fluidly connected between the chemical reservoirs 36 and the nozzles 38 to force the substances from the reservoirs 36 through the nozzles 38. In the embodiment shown, the dispersion system includes a pump 42, an air pressure regulator 44, and an air compressor 46. The chemical dispersion assembly 34 may also include a drain 48 to drain substances from the reservoirs 36.

In some embodiments, the one or more nozzles 38 include atomizing nozzles that are configured to transform the disinfecting substance at the input of the one or more nozzles 38 to a fog at the output of the one or more nozzles 38. In some embodiments, the one or more nozzles 38 are disposed on the top of the housing 12 relative to the air dispersion outlet 16 such that the generated fog impinges on the air flow from the air dispersion outlet 16. In other embodiments, one or more nozzles 38 are disposed in the interior of the housing 12. In further embodiments, one or more nozzles 38 are disposed on other external sides of the housing 12.

To produce the fog, the atomizing nozzle 38 may generate fine droplets of the disinfecting substance. In one embodiment, the droplets of disinfecting substance generated by the nozzle 38 average less than about 10 μm. Although larger droplets can be employed, droplets of this size allow for even dispersion and avoid excessive condensation, corrosion, and surface wetting issues in the interior of the housing 12 and the room being disinfected. In addition, some amount of the small droplets can evaporate such that the vapor portion of the fog penetrates less accessible areas. It will be appreciated that the droplet size and the amount of surfactant dispersed can be selected to provide the desired level of surface wetting in the room. The droplet size can be controlled by changing the pressure by which the disinfecting substance is forced through the nozzle 38, the air pressure that forces the disinfecting substance through the nozzle 38 (as controlled by the dispersion system), and/or by changing the size of the nozzle 38. The selection of droplet size may be based on the ambient conditions of the room to be disinfected (e.g., temperature, humidity, etc.) and the desired level of coverage in the room with the disinfecting substance and/or antimicrobial coating substance. One exemplary nozzle 38 that may be suitable for use in the chemical dispersion assembly 34 is a nozzle such as that used in the Minncare Dry Fog® or Mini Dry Fog systems, sold by Mar Cor Purification, Shippack Pa. Another example nozzle that may be suitable for use in the chemical dispersion assembly 34 is a spray nozzle assembly including Spraying Systems Co. product numbers 1/4J-316SS, SU1A-316SS, and 46138-16-316SS, sold by Spraying Systems Co., Wheaton, Ill.

A bottom inlet cover assembly 50 is disposed between the bottom air inlet 22 and the interior of the housing 12. In some embodiments, the bottom inlet cover assembly 50 includes a plurality of parallel rotatable louvers 52.

Figure 4:
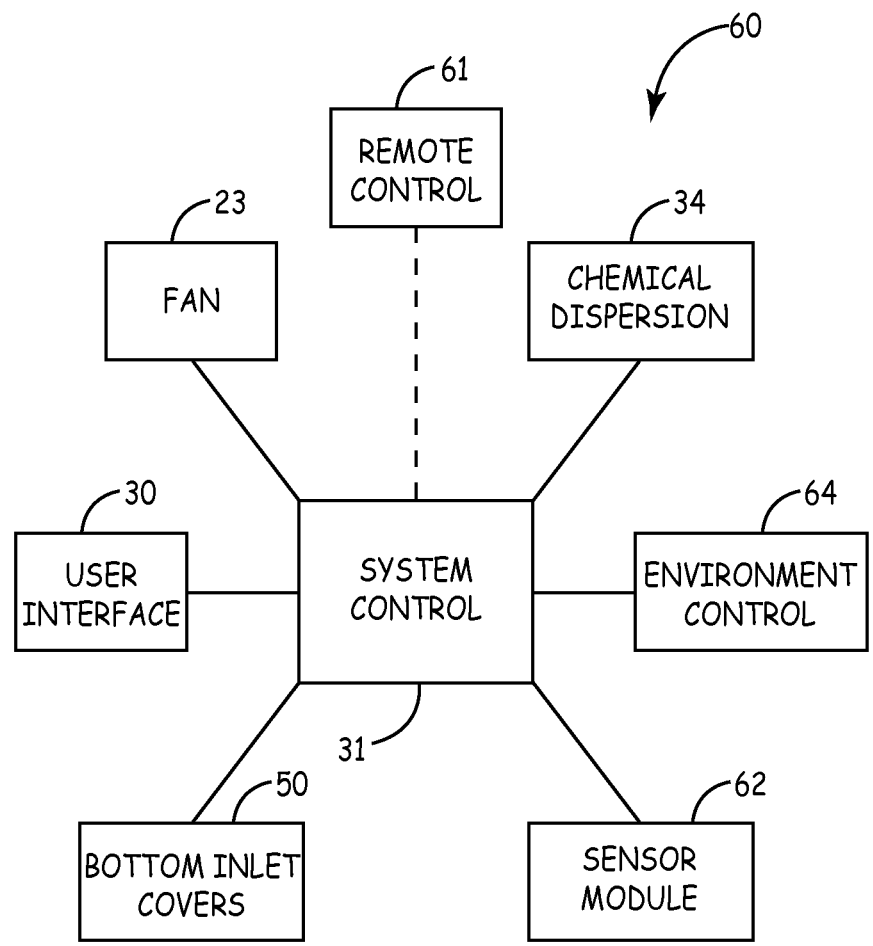
FIG. 4 is a block diagram of an embodiment of a control system for the system shown in FIGS. 1-3.

FIG. 4 is a block diagram of an embodiment of a control system 60 that is configured to control operation of the system 10 shown in FIGS. 1-3. The control system 60 includes the system controller 31 that controls operation of the fan 23, a chemical dispersion assembly 34, and the bottom inlet cover assembly 50. The control system 60 also includes a remote control 61 that is operable to control operation of the system control 31 from a remote location. Also shown in FIG. 4 is a sensor module 62 and an environmental control system 64, which are also controlled by the system controller 31. The sensor module 62 and the environmental control system 64, which will be described in more detail herein, may be incorporated into the system 10. The control system 60 receives signals from and, in some cases, sends signal to the user interface 30.

Figure 5:
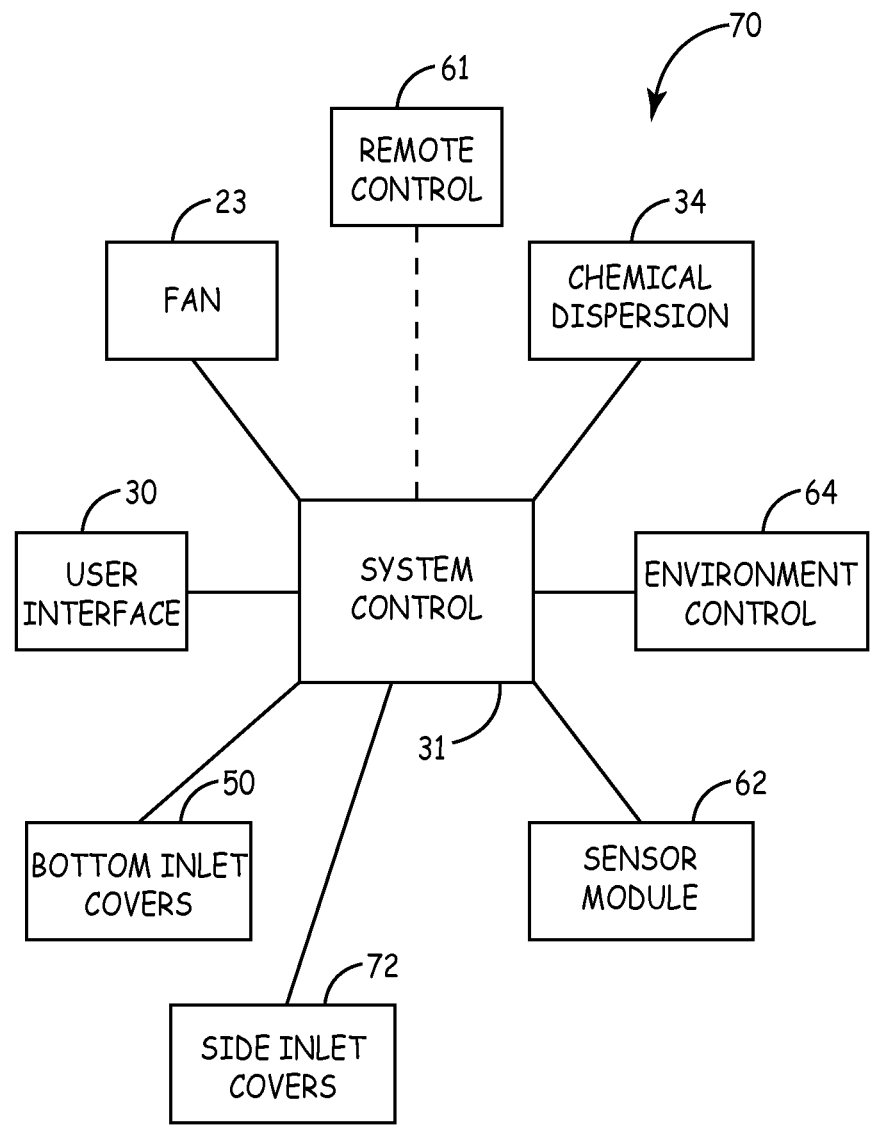
FIG. 5 is a block diagram of another embodiment of a control system for the system shown in FIGS. 1-3.

FIG. 5 is a block diagram of another embodiment of a control system 70 that is configured to control operation of the system 10 shown in FIG. 1. Similar to the control system 60 shown in FIG. 4, the control system 70 includes a system controller 31 that controls operation of the fan 23, a chemical dispersion assembly 34, a bottom inlet cover assembly 50, a sensor module 62, and an environmental control system 64, and a remote control 61 that is operable to control operation of the system control 31 from a remote location. In this embodiment, the control system 70 also includes a side inlet cover assembly 72. The components of control systems 60 and 70 will be described in more detail below.

The bottom inlet cover assembly 50 is disposed between the bottom air inlet 22 and the interior of the housing 12, and is configured to control the air that flows through the bottom air inlet 22. As discussed above, in some embodiments, the bottom inlet cover assembly 50 includes a plurality of parallel rotatable louvers 52. The system controller 31 may be configured to rotate each of the louvers 52 about its longitudinal axis to actuate the bottom inlet cover assembly 50 between its open and closed states. In alternative embodiments, the bottom inlet cover assembly 50 has other configurations that provide controllable air flow through the bottom air inlet 22. For example, the bottom inlet cover assembly 50 may comprise trapdoor-like assemblies sized to cover the air inlet 22.

The side inlet cover assembly 72 is disposed between the side air inlets 20 and the interior of the housing 12. The side inlet cover assembly 72 is configured to control the air that flows through the side air inlets 20. The side inlet cover assembly 72 and bottom inlet cover assembly 50 are independently controllable and actuatable. In some embodiments, the side inlet cover assembly 72 and bottom inlet cover assembly 50 each include a plurality of parallel rotatable louvers. The system controller 31 may be configured to rotate each of the louvers about its longitudinal axis to actuate the inlet cover assemblies 50, 72 between their open and closed states. In alternative embodiments, the side inlet cover assembly 72 and/or the bottom inlet cover assembly 50 have other configurations that provide controllable air flow through the side air inlets 20 and bottom air inlet 22, respectively. For example, the side inlet cover assembly 72 and/or bottom inlet cover assembly 50 may comprise trapdoor-like assemblies sized to cover the air inlets 20, 22.

The system 10 is prepared for operation by filling the chemical reservoirs of the chemical dispersion assembly 34 with the desired substances and transporting the system 10 to the desired location. For example, as discussed above, one chemical reservoir 36 may be filled with a disinfecting substance and another chemical reservoir 36 may be filled with a longer duration antimicrobial coating substance, the two substances may be combined in a single reservoir 36, or the substances may be mixed just prior to or during dispersement. A surfactant may be combined with the disinfecting substance or added to one of the chemical reservoirs 36. The user interface 30 may then be used to initiate operation of the system 10 to begin the disinfection process. In some embodiments, a button is pressed on the user interface 30, and the system controller 31 waits a predetermined period of time before starting the process to allow the user to exit the room. For example, in embodiments of the system 10 including a remote control interface, the disinfection process may be initiated by pressing one or more buttons on the remote control 61. In alternative embodiments, the sensor module 62 may include one or more status sensors, such as motion, heat sources, and/or other sensors, in communication with the system controller 31 that prevents the system 10 from initiating while the sensors detect activity in the room.

The sensor module 62 may also include one or more ambient condition sensors that sense the conditions of the room to be disinfected prior to the disinfection process. For example, the efficacy of the disinfecting substance and/or the antimicrobial coating substance (the latter discussed in more detail below) may be affected by the temperature and/or humidity of the room. Thus, in some embodiments, the sensor module 62 includes temperature and/or humidity sensors that provide signals to the system controller 31 relating to the temperature and humidity of the room. If the sensor module 62 senses conditions that are not suitable or ideal for disinfection of the room, the system controller 31 may prevent the system from initiating the process, and may indicate which conditions are less than satisfactory on the user interface 30.

The system 10 may also include an environment control system 64 that allows the system 10 to adjust the room conditions to a satisfactory state before or during the disinfection process. For example, the environment control system 64 may include integrated heaters that are activated by the system controller if the room is too cold to disperse the disinfecting substance and/or the antimicrobial coating substance. The environment control system 64 may also include a humidifier or dehumidifier that may be activated by the system controller 31 to adjust the humidity to satisfactory levels prior to initiating the process or during the process. Alternatively, the environment control system 64 may be configured to mix water with the disinfecting substance to increase the humidity of the room while dispersing the disinfecting substance.

The system controller 31 may delay activation of the disinfecting process until the environment control system 64 adjusts ambient conditions in the room to threshold ambient conditions. The threshold ambient conditions, which may be programmed in the system controller 31, may be set to increase the efficacy of the disinfecting substance and/or antimicrobial coating substance.

Figure 6:
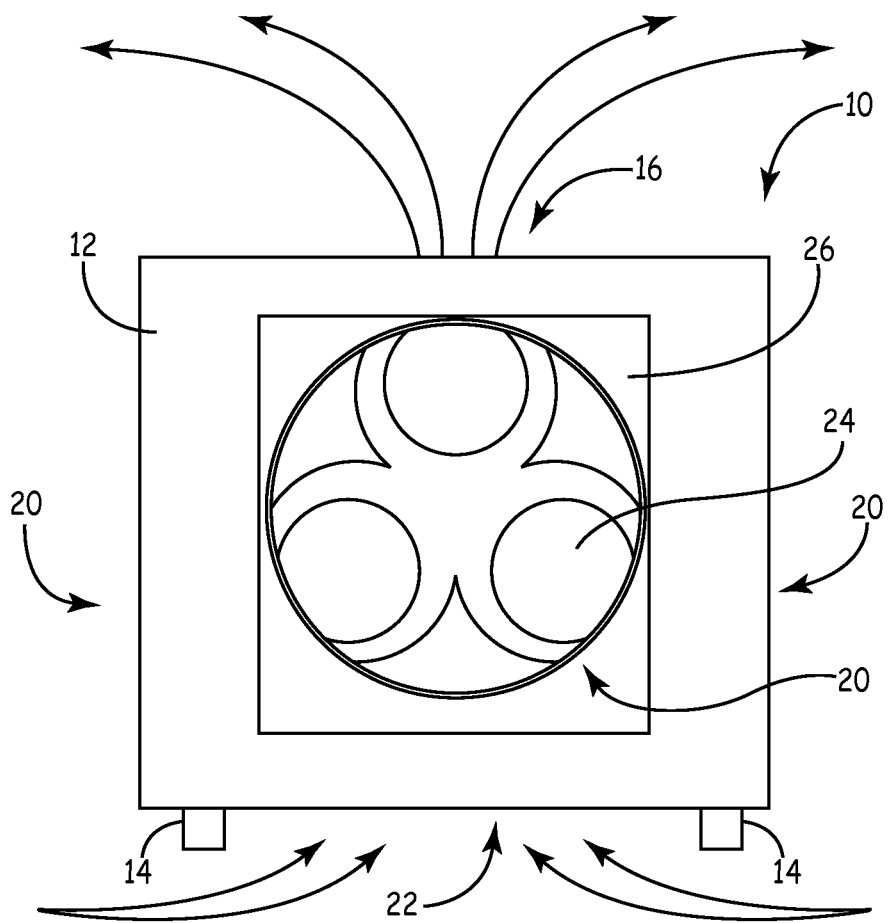
FIG. 6 is a diagrammatic view of the system shown in FIGS. 1-3, illustrating air flow when the system is dispersing disinfecting fog into the room.
Figure 7:
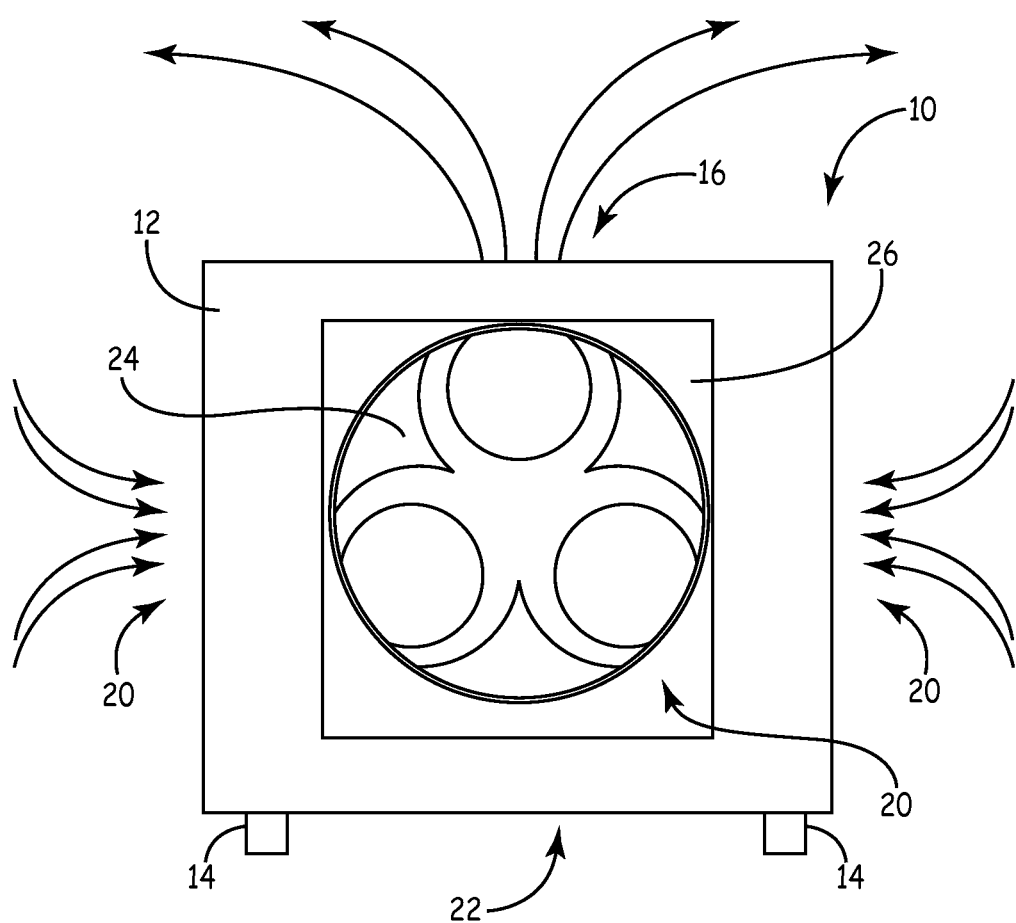
FIG. 7 is a diagrammatic view of the system shown in FIGS. 1-3, illustrating air flow when the system is drawing the disinfecting fog from the room and through filters for vapor destruction.

If the system controller 31 determines that ambient conditions are satisfactory based on signals from the sensor module 62, the system 10 may then begin the process of disinfecting the room. In the control system 60, the bottom inlet cover assembly 50 is opened, which causes most air to flow into the housing 12 via the bottom air inlet 22 due to the presence of the filters 24 at the side air inlets 20. That is, the air flow through the side inlets 20 is impeded by the filters 24, and thus most air is drawn into the housing 12 through the bottom air inlet 22. The fan 23 is then activated to begin pulling air through the housing 12 via the bottom air inlet 22, as illustrated in FIG. 6.

In the control system 70 in FIG. 5, the side inlet cover assembly 72 is closed to prevent air flow through the side air inlets 20, and the bottom inlet cover assembly 50 is opened to allow air to flow through the bottom air inlet 22. The fan 23 is then activated to begin pulling air through the housing 12 via the bottom air inlet 22, as illustrated in FIG. 6.

The system 10 then disperses the disinfecting substance into the room to be disinfected. The system controller 31 commands the chemical dispersion assembly 34 to begin dispensing the disinfecting substance relative to the air dispersion assembly 16. For example, in embodiments in which the disinfecting substance is transformed into a fog as described above, the chemical dispersion assembly 34 forces the disinfecting substance through one or more atomizing nozzles 38 to generate the fog near the fan 23. As the fog is generated, the fog impinges the air flow from the air dispersion outlet 16 for dispersion into the room to be disinfected. The fan 23 continues to operate while the chemical dispersion assembly 34 disperses the fog for a predetermined time. This predetermined time may be based on the size of the room to be disinfected, for example. In some embodiments, the amount of time that the chemical dispersion assembly 34 disperses the disinfecting substance while the fan 23 is operating is based on a program selected via the user interface 30. The system 10 may also include one or more sensors that monitor the concentration of the disinfecting substance in the room and alert the system controller 31 when the programmed concentration is reached.

In some embodiments, the fog is then held in the room for a predetermined time. During this hold time, the fan 23 may continue to run with the bottom inlet cover 48 open to circulate the fog through the room. The predetermined time may be programmed into the system controller 31 and may be based on the size of the room being disinfected. The time may also be determined based on room conditions such as temperature, fog concentration, and humidity that are sensed by the sensor module 62 before or during the disinfection process. This is because the temperature, concentration, and/or humidity can affect the time it takes to reach the desired level of decontamination.

When dispersion of the fog is completed, the system controller 31 closes the bottom inlet cover assembly 50. In the control system 70, the system controller 31 also opens the side inlet cover assembly 72. In both control systems 60 and 70, this arrangement prevents air flow through the bottom air inlet 22 and causes air from the room to be drawn through the filters 24 and the side air inlets 20 into the housing 12, as illustrated in FIG. 7. The filters 24 neutralize and/or capture vapors of the fog before it passes into the interior of the housing 12. In some embodiments, the filters 24 are carbon based filters. In other embodiments, the filters 24 are zeolite filters, molecular sieves, or silica filters. The filters 24 may also be configured to chemically destroy the fog as it passes through the filters 24. For example, the filters 24 may be treated with a substance such as potassium permanganate ($KMnO_4$). The filters 24 may further be configured to include a desiccant.

After passing through the filters 24, the air in the interior of the housing 12 is substantially free of the disinfecting substance. This air is redistributed into the room through the air dispersion outlet 16 by the fan 23. This process reduces the concentration of the disinfecting substance in the room. The fan 23 continues to circulate the air in the room through the filters 24 for a predetermined time to remove substantially all of the disinfecting substance from the room. The predetermined time may be based on the size of the room, and/or may be based on a program selected via the user interface 30.

As discussed above, the sensor module 62 may include one or more sensors that provide signals to the system controller 31 related to the concentration of the disinfecting substance in the room. In this case, the system controller 31 can continue to run the fan 23 until the concentration of the disinfecting substance gets to suitable levels. The system 10 can also provide visual and/or audible indicators (e.g., via the user interface 30 or the remote control 61) during vapor destruction until the disinfecting substance concentration reaches the suitable levels.

During or following dispersion of the disinfecting substance, the system 10 may optionally disperse an antimicrobial coating substance that coats surfaces in the room. In addition, the system controller 31 may operate the environment control system 64 to adjust room conditions if preferred ambient conditions are different for the antimicrobial coating. The antimicrobial coating remains on the surfaces so as to extend the time that the room remains clean after the disinfection process. One exemplary substance suitable for use as an antimicrobial coating is disclosed in U.S. Pat. No. 4,259,103, entitled "Method of Reducing the Number of Microorganisms in a Media and a Method of Preservation," which is incorporated herein by reference in its entirety.

To distribute the antimicrobial coating substance, the system controller 31 opens the bottom inlet cover assembly 50 to allow air to flow through the bottom air inlet 22, as illustrated in FIG. 6. In control system 70, the system controller 31 also closes the side inlet cover assembly 72 to prevent air flow through the side air inlets 20. The system controller 31 then commands the chemical dispersion assembly 34 to dispense the antimicrobial coating substance relative to the air dispersion outlet 16. The antimicrobial coating substance may be forced through the nozzles 38 of the chemical dispersion assembly 34 to disperse the antimicrobial coating as a fog. The antimicrobial coating substance is dispersed by the fan 23 into the room. The fan 23 continues to operate while the chemical dispersion assembly 34 dispenses the antimicrobial coating substance for a predetermined time. In some embodiments, the disinfecting substance and the antimicrobial coating substance are dispersed into the room sequentially. In other embodiments, the disinfecting substance and the antimicrobial coating substance are dispersed into the room simultaneously. In further embodiments, the disinfecting substance is dispersed for a period of time before the antimicrobial coating substance is dispersed, and then the disinfecting and antimicrobial coating substances are dispersed simultaneously.

In some embodiments, the antimicrobial coating substance is then held in the room for a predetermined time to allow the antimicrobial coating substance to coat the surfaces of the room. During this hold time, the fan 23 may continue to run with the bottom inlet cover assembly 50 open to circulate the fog through the room. Alternatively, the fan 23 may be disabled during the hold time. The predetermined time may be programmed into the system controller 31 and may be based on the size of the room being disinfected. The time may also be determined based on room conditions such as temperature and humidity that are sensed before or during the disinfection process. This is because the temperature and/or humidity can affect the ability of the antimicrobial substance to bond to surfaces in the room.

After dispersion of the antimicrobial coating substance, the system controller 31 may close the bottom inlet cover assembly 50 (and, in the control system 70, open the side inlet cover assembly 72) to draw air from the room through the filters 24 and the side air inlets 20 into the housing 12. This removes the antimicrobial coating substance from the air in the room. In an alternative embodiment, the system 10 includes different filters or different substances within the same filters for the destruction of the disinfecting substance and antimicrobial substance. When the antimicrobial substance has been drawn from the room, the disinfection process ends and the system controller 31 disables components of the system 10, including the chemical dispersion system 44 and the fan 23. The system controller 31 may also open or close the bottom inlet cover assembly 50 (and, in the control system 70, open or close the side inlet cover assembly 72) at the end of the cycle. In some embodiments, the system 10 further provides an audible and/or visual signal that indicates that the system 10 has completed the disinfecting cycle.

In summary, the present invention relates to a system for disinfecting a room including an enclosure having first and second air inlets, and an air intake control assembly configured for selectable control of air flow between an exterior and an interior of the enclosure through the first and second air inlets. A filter assembly is disposed relative to the second air inlet such that air that flows between the exterior and interior of the enclosure through the second air inlet passes through the filter assembly. An air dispersion outlet including a fan is configured to draw air into the enclosure through the first and second air inlets and to force air out of the enclosure. A chemical dispersion assembly is configured to generate a disinfecting fog relative to the air dispersion outlet. A system controller is configured to open the first air inlet and activate the fan to disperse the disinfecting fog into the room, and subsequently close the first air inlet to draw the disinfecting fog from the room and through the filter assembly. The system as described is capable of disinfecting substantially all surfaces in the room quickly and automatically.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof. For example, while the system 10 has been described as a portable box-like assembly, it will be appreciated that other configurations are also possible, such as ceiling mounted, door mounted, or wall mounted configurations.

What is claimed is:

1. A system for disinfecting a room, the system comprising:
   an enclosure including first and second air inlets;
   an air intake control assembly configured for selectable control of air flow between an exterior and an interior of the enclosure through the first and second air inlets;
   a disinfecting substance filter assembly disposed relative to the second air inlet such that air that flows between the exterior and interior of the enclosure through the second air inlet passes through the disinfecting substance filter assembly;
   an air dispersion outlet including a fan configured to draw air into the enclosure through the first and second air inlets and to force air out of the enclosure;
   a chemical dispersion assembly configured to generate a disinfecting fog relative to the air dispersion outlet via an atomizer; and
   a system controller programmed to open the first air inlet and activate the fan to disperse the disinfecting fog into the room, and subsequently close the first air inlet to draw the disinfecting fog from the room and through the second air inlet and the disinfecting substance filter assembly,
   wherein the chemical dispersion assembly comprises:
   a chemical reservoir configured to retain a disinfecting substance;
   a first atomizing nozzle configured to transform the disinfecting substance into the disinfecting fog;
   a second atomizing nozzle; and
   a third atomizing nozzle, and wherein the first, second and third atomizing nozzles are spaced on different sides of the air dispersion outlet external of the enclosure.

2. The system of claim 1, wherein the air intake control assembly comprises:
   a first air inlet cover assembly having an open state, which permits air flow between an exterior of the enclosure and an interior of the enclosure via the first air inlet, and a closed state, which prevents air flow between the exterior and interior of the enclosure via the first air inlet and allows air flow between the exterior and interior of the enclosure via the second air inlet.

3. The system of claim 2, and further comprising:
   a second air inlet cover assembly having an open state, which permits air flow between an exterior of the enclosure and an interior of the enclosure via the second air inlet, and a closed state, which prevents air flow between the exterior and interior of the enclosure via the second air inlet.

4. The system of claim 1, and further comprising:
   an antimicrobial dispersion assembly configured to dispense an antimicrobial coating substance relative to the air dispersion outlet, wherein the system controller is further configured to open the first air inlet and activate the fan to disperse the antimicrobial coating substance into the room.

5. The system of claim 4, wherein the antimicrobial coating substance is dispersed simultaneously with the disinfecting substance.

6. The system of claim 1, wherein a surfactant is dispersed before or during dispersion of the disinfecting fog.

7. The system of claim 1, and further comprising:
one or more ambient condition sensors configured to sense ambient conditions in the room.

8. The system of claim 7, wherein the one or more ambient condition sensors are configured to sense one or more of heat sources, humidity, motion, and temperature.

9. The system of claim 7, and further comprising:
an environment control system configured to alter conditions in the room based conditions sensed by the one or more ambient condition sensors.

10. The system of claim 1, wherein air flow from the first air inlet substantially bypasses the disinfecting substance filter assembly.

11. The system of claim 1, wherein the system is sized and configured to be transported into the room to be disinfected and transported out of the room after disinfection.

12. The system of claim 1, wherein the enclosure contains the disinfecting substance filter assembly, the fan, and the system controller.

13. The system of claim 1, wherein the air dispersion outlet is configured to spread the air and fog in opposite directions throughout the room.

14. The system of claim 1, wherein the second air inlet comprises first and second side inlets positioned on opposite sides of the enclosure.

15. The system of claim 1, wherein the disinfecting substance filter assembly chemically destroys both peracetic acid and hydrogen peroxide passing therethrough.

16. The system of claim 1, wherein the disinfecting substance filter assembly comprises a disinfecting substance filter that neutralizes or captures disinfecting substance passing therethrough.

17. A system for disinfecting a room, the system comprising:
an enclosure including first and second air inlets;
a plurality of controllable louvers arranged to control of air flow between an exterior and an interior of the enclosure through the first air inlet;
a disinfecting substance destruction assembly disposed relative to the second air inlet such that air that flows between the exterior and interior of the enclosure through the second air inlet passes through the disinfecting substance destruction assembly;
an air dispersion outlet including a fan configured to draw air into the enclosure through the first and second air inlets and to force air out of the enclosure;
a chemical dispersion assembly configured to generate a disinfecting fog relative to the air dispersion outlet via an atomizer; and
a system controller programmed to open the first plurality of louvers and activate the fan to disperse the disinfecting fog into the room, and to subsequently close the first plurality of louvers and activate the fan to draw the disinfecting fog from the room and through the second air inlet and the disinfecting substance destruction assembly, wherein the chemical dispersion assembly comprises:
a chemical reservoir configured to retain a disinfecting substance;
a first atomizing nozzle configured to transform the disinfecting substance into the disinfecting fog;
a second atomizing nozzle; and
a third atomizing nozzle, and wherein the first, second and third atomizing nozzles are spaced on different sides of the air dispersion outlet external of the enclosure.

18. The system of claim 17, wherein the chemical dispersion assembly comprises
a chemical reservoir configured to retain a disinfecting substance; and
an atomizing nozzle that transforms the disinfecting substance into the disinfecting fog.

19. The system of claim 17, and further comprising:
an antimicrobial dispersion assembly configured to dispense an antimicrobial coating substance relative to the air dispersion outlet, wherein the system controller is further configured to open the first plurality of louvers and activate the fan to disperse the antimicrobial coating substance into the room.

20. The system of claim 17, and further comprising:
one or more ambient condition sensors configured to sense ambient conditions in the room.

21. The system of claim 20, and further comprising:
an environment control system configured to alter conditions in the room based conditions sensed by the one or more ambient condition sensors.

22. A system for disinfecting a room, the system comprising:
an enclosure including first and second air flow paths;
an air flow control assembly configured for selectable control of air flow through the first and second air flow paths;
a disinfecting substance destruction assembly disposed in the second air flow path;
at least one air dispersion outlet;
a fan configured to flow air into the enclosure, through the first and second air flow paths, and out through the at least one air dispersion outlet;
a chemical dispersion assembly configured to generate a disinfecting fog relative to the air dispersion outlet via an atomizer; and
a system controller programmed to control operation of the fan, the air flow control assembly, and the chemical dispersion assembly so as to generate the disinfecting fog and to flow air through the first air flow path, bypassing the disinfecting substance destruction assembly, and out through the at least one air dispersion outlet in a disinfection process and subsequently to cease generation of the disinfecting fog and to flow air through the second air flow path, bypassing the first air flow path, to destroy the disinfecting fog via the disinfecting substance destruction assembly, wherein the chemical dispersion assembly comprises:
a chemical reservoir configured to retain a disinfecting substance;
a first atomizing nozzle configured to transform the disinfecting substance into the disinfecting fog;
a second atomizing nozzle; and
a third atomizing nozzle, and wherein the first, second and third atomizing nozzles are spaced on different sides of the air dispersion outlet external of the enclosure.

23. The system of claim 22, wherein the disinfecting substance destruction assembly is configured for chemically destroying both peracetic acid and hydrogen peroxide.

24. The system of claim 22, wherein the disinfecting substance destruction assembly comprises a potassium permanganate chemical destruction filter.

25. The system of claim 22, wherein the air dispersion outlet is oriented and configured to spread the air and fog in opposite directions throughout the room.

26. The system of claim 22, wherein the air dispersion outlet is oriented and configured to spread the air and fog in 360 degrees.

27. The system of claim 22, wherein the first air flow path extends from a first air inlet to the at least one air dispersion outlet and the second air flow path extends from a second air inlet to the at least one air dispersion outlet.

28. The system of claim 22, wherein the fog comprises droplets sized for wetting surfaces in the room as well as a portion of evaporated vapor.

29. The system of claim 22, and further comprising:
- a humidity sensor connected to the system controller, wherein the system controller ends the disinfection process at a time determined based on room humidity data sensed by the humidity sensor.

* * * * *